United States Patent [19]
Ryatt et al.

[11] Patent Number: 6,047,699
[45] Date of Patent: Apr. 11, 2000

[54] VENTILATOR AND TRACH HOLDER DEVICE

[75] Inventors: Sadie Ryatt, Santa Clarita; Stacie Orr, Newhall, both of Calif.

[73] Assignee: The Ryatt Corporation, Reno, Nev.

[21] Appl. No.: 09/178,368

[22] Filed: Oct. 23, 1998

[51] Int. Cl.$^7$ .............................. A61M 16/00; A61M 5/32
[52] U.S. Cl. ............ 128/207.17; 128/912; 128/DIG. 26; 604/174; 604/179
[58] Field of Search ........................ 128/200.26, 202.16, 128/202.27, 207.14, 207.17, 912, DIG. 15, DIG. 26, 207.29; 604/174, 179, 180; 623/9

[56] References Cited

U.S. PATENT DOCUMENTS

| | | | |
|---|---|---|---|
| 3,927,676 | 12/1975 | Schultz | 128/DIG. 26 |
| 4,548,200 | 10/1985 | Wapner | 128/207.17 |
| 5,038,778 | 8/1991 | Lott | 128/207.17 |
| 5,135,506 | 8/1992 | Gentelia et al. | 604/180 |
| 5,282,463 | 2/1994 | Hammersley | 128/207.15 |
| 5,357,952 | 10/1994 | Schuster et al. | 128/207.17 |
| 5,433,195 | 7/1995 | Kee et al. | 128/207.14 |
| 5,437,273 | 8/1995 | Bates et al. | 128/207.17 |
| 5,507,285 | 4/1996 | Mota | 128/207.17 |
| 5,546,938 | 8/1996 | McKenzie | 128/207.17 |
| 5,551,421 | 9/1996 | Noureldin et al. | 128/207.17 |
| 5,555,881 | 9/1996 | Rogers et al. | 128/207.17 |
| 5,924,421 | 7/1999 | Rosbrook et al. | 128/207.14 |

*Primary Examiner*—John G. Weiss
*Assistant Examiner*—Todd M. Martin
*Attorney, Agent, or Firm*—John K. Flanagan; John R. Flanagan; Flanagan & Flanagan

[57] ABSTRACT

A ventilator and trach holder device includes a main attachment body and at least one and, preferably, a pair of spaced apart attachment tab members. The main attachment body includes a central panel, a pair of spaced apart first connection members, a pair of spaced apart second connection members and a plurality of patches of complementary mateable hook and loop fastener material. The first and second connection members and central panel provide the main attachment body with a H-shaped configuration and the patches are complementary to and mateable with one another such that the main attachment body may be wrapped around a ventilator circuit component and held in place by fastening the patches to one another. Each attachment tab member includes opposite first and second ends and a pair of patches of complementary and mateable hook and loop fastener material. The first end of the attachment tab member is mounted to the central panel of the main attachment body. The patches are complementary to and mateable with one another such that the attachment tab member may be inserted through a slot in and extended around a side of a trach assembly plate and fastened onto itself by fastening the patches to one another so as to hold the trach assembly plate in place in relation to the ventilator circuit component. Each attachment tab member includes an elastic portion at an intermediate position to permit stretching of the attachment tab member.

20 Claims, 2 Drawing Sheets

VENTILATOR AND TRACH HOLDER DEVICE

BACKGROUND OF THE INVENTION

1. Field of the Invention

The present invention generally relates to medical appliances and, more particularly, is concerned with a ventilator and trach holder device.

2. Description of the Prior Art

A person may require assistance in the process of breathing. A ventilator circuit and tracheostomy tube (or trach) assembly may be employed to provide such assistance. The ventilator circuit or trach assembly, however, may become inadvertently disconnected from a patient during suctioning of the trach assembly or during patient agitation or by other means. Such inadvertent disconnection may result in the deprivation of oxygen, inadequate ventilation and/or possible death. A variety of devices have therefore been developed over the years to prevent disconnection.

Representative examples of these prior art devices are disclosed in U.S. Pat. No. 4,548,200 to Wapner, U.S. Pat. No. 5,038,778 to Lott, U.S. Pat. No. 5,282,463 to Hammersley, U.S. Pat. No. 5,357,952 to Schuster et al., U.S. Pat. No. 5,546,938 to McKenzie, U.S. Pat. No. 5,551,421 to Noureldin et al. and U.S. Pat. No. 5,555,881 to Rogers et al. While these prior art devices appear to be satisfactory for the specific purposes for which they were designed, none of them seem to provide an effective and comprehensive solution for the problem at hand.

Consequently, a need still exists for a device which provides an optimum solution to the aforementioned problem in the prior art without introducing any new problems in place thereof.

SUMMARY OF THE INVENTION

The present invention provides a ventilator and trach holder device which is designed to satisfy the aforementioned need. The ventilator and trach holder device of the present invention is intended to prevent inadvertent disconnection of the ventilator circuit or trach assembly from a patient. The holder device is particularly designed for attachment to a component of the ventilator circuit and a plate of the trach assembly. The holder device retains the ventilator circuit component and trach assembly plate in place during suctioning of the trach assembly and during patient agitation and when other forces are applied to either of the ventilator circuit component and trach assembly plate.

Accordingly, the present invention is directed to a ventilator and trach holder device which comprises: (a) a main attachment body including (i) a central panel having opposite ends and opposite sides, (ii) a pair of first connection members laterally spaced apart from one another along and attached to and extending in first directions from one of the opposite ends of the central panel and disposed adjacent to the opposite sides thereof, each of the first connection members having an end, (iii) a pair of second connection members laterally spaced apart from one another along and attached to and extending in second directions opposite the first directions from the other of the opposite ends of the central panel and disposed adjacent to the opposite sides thereof, each of the second connection members having an end, and (iv) means for fastening the ends of the first and second connection members to one another such that the main attachment body will wrap around a ventilator circuit component and be held in place by the fastening means; and (b) at least one attachment tab member including (i) opposite first and second ends, the first end being mounted to the central panel of the main attachment body and extending along the connection members of one of the pairs thereof, and (ii) means for fastening the second end of the attachment tab member to a portion of the attachment tab member such that the attachment tab member may be inserted through a slot in and extended around a side of a plate of a trach assembly and fastened onto itself so as to hold the trach assembly plate in place in relation to the ventilator circuit component. The first and second of connection members of the main attachment body are aligned with the respective opposite sides of the central panel and together therewith provide the main attachment body with a substantially H-shaped configuration.

Each of the first and second connection members of the main attachment body preferably have substantially the same dimensions. Each of the first and second connection members of the main attachment body has a length and a width. The attachment tab member also has a length and a width. The length of the attachment tab member is substantially greater than the length of each of the first and second connection members of the main attachment body. The width of each of the first and second connection members of the main attachment body is substantially greater than the width of the attachment tab member.

The fastening means of the main attachment body includes a plurality of patches of complementary mateable hook and loop fastener material. Each patch is affixed to an end of a connection member. The patches of the first connection members have the same type of fasteners and the patches of the second connection members have the same type of fasteners complementary to and mateable with the fasteners on the patches of the first connection members. The fastening means of the attachment tab member includes a pair of patches of complementary and mateable hook and loop fastener material. A first patch is affixed at an intermediate position on the attachment tab member and has one type of fastener. A second patch is affixed to the second end of the attachment tab member and has the complementary type of fastener mateable with the fasteners on the first patch of the first connection members. The attachment tab member includes an elastic portion at an intermediate position to permit stretching of the attachment tab member. Preferably, a pair of the attachment tab members is provided in the holder device.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

DETAILED DESCRIPTION OF THE INVENTION

Figure 1:
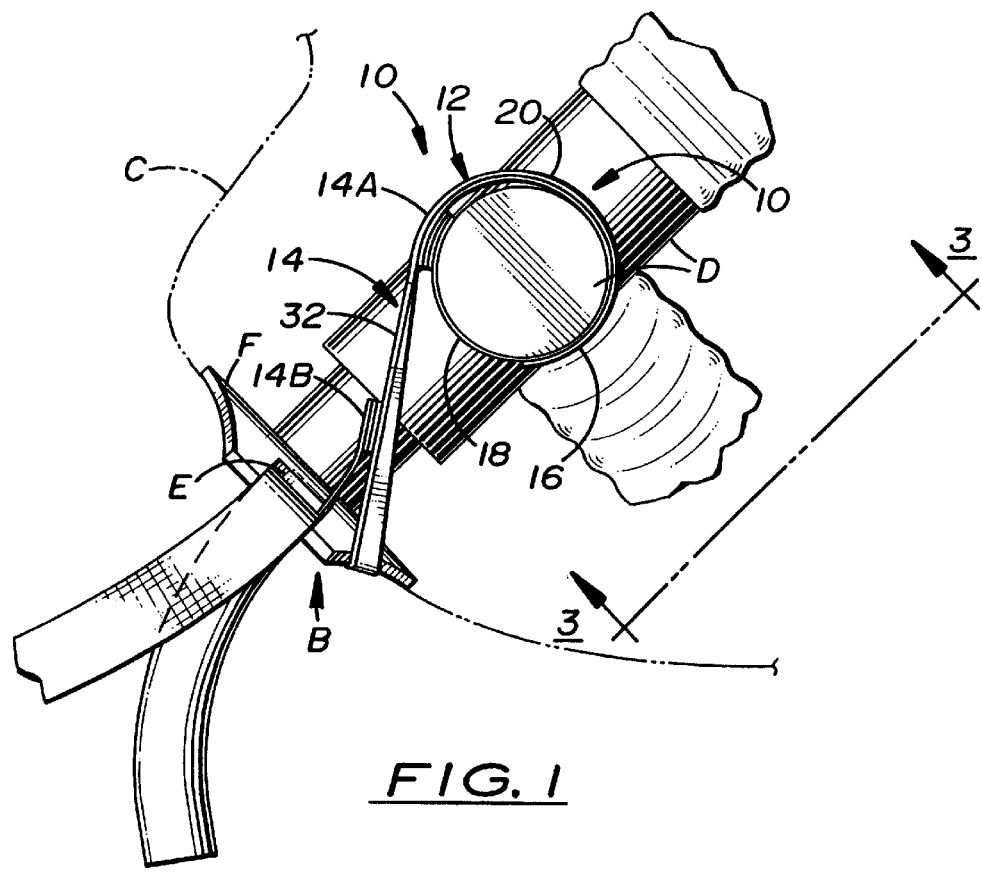
FIG. 1 is a side elevational view of a ventilator and trach holder device of the present invention shown holding a ventilator circuit component and trach assembly plate in place.
Figure 2:
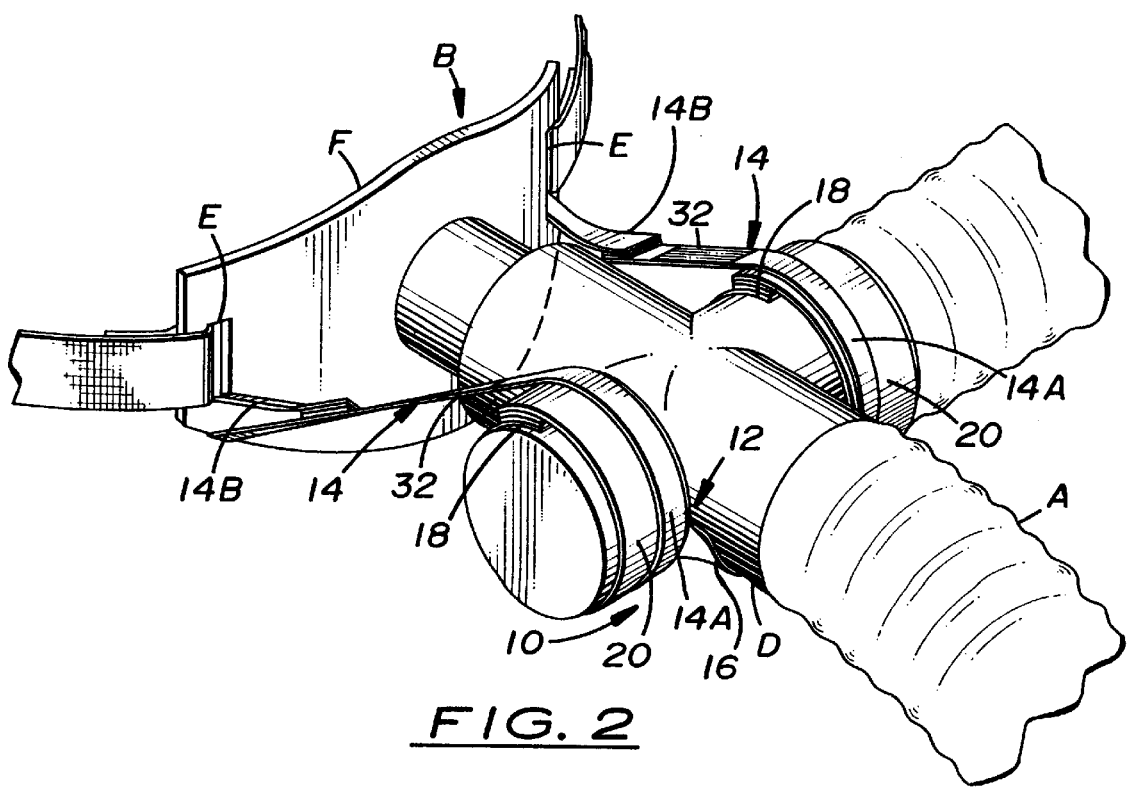
FIG. 2 is a pespective view of the holder device of FIG. 1.
Figure 4:
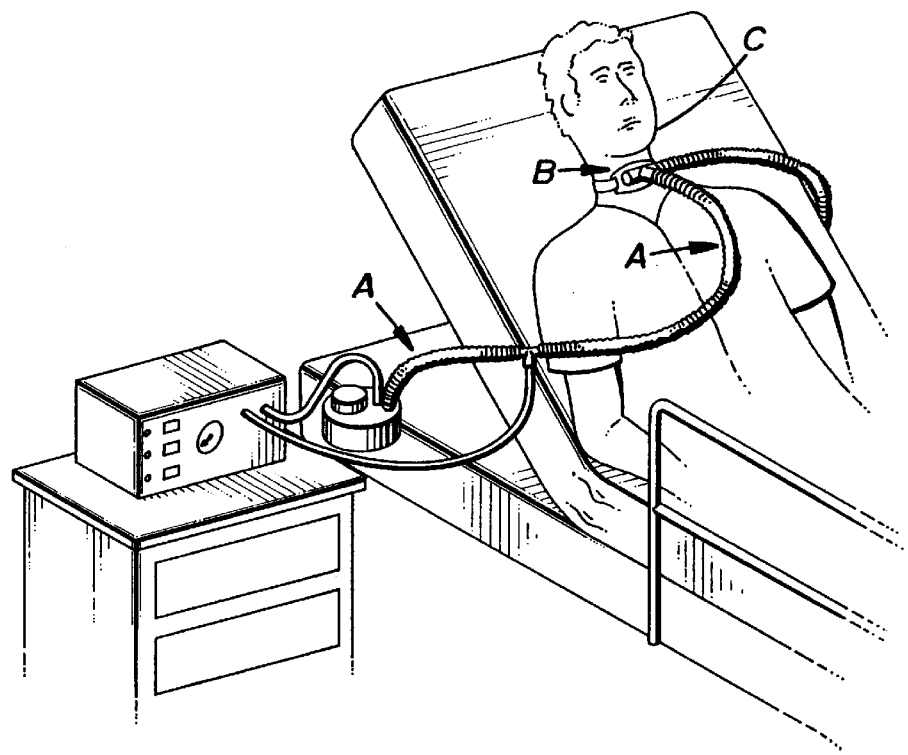
FIG. 4 is a perspective view of the holder device of FIGS. 1 to 3 shown in conjunction with a ventilator circuit and trach assembly connected to a patient.

Referring to the drawings and particularly to FIGS. 1 and 2, there is illustrated a ventilator and trach holder device, generally designated 10, of the present invention. As shown in FIG. 4, the ventilator and trach holder device 10 of the present invention is intended to be used in conjunction with a ventilator circuit A and a trach assembly B connected to a patient C.

Basically, the ventilator and trach holder device 10 includes a main attachment body 12 and at least one and, preferably, a pair of spaced apart attachment tab members 14. The main attachment body 12 includes a central panel 16, a pair of laterally spaced apart first connection members 18, a pair of laterally spaced apart second connection members 20 and a fastening means 22. The central panel 16 has opposite ends 16A, 16B and opposite sides 16C, 16D. The first connection members 18 are laterally spaced apart along, and attached to and extend in first directions from, the opposite end 16A of the central panel 16. The first connection members 18 are disposed substantially in parallel relationship with one another and adjacent to, and preferably in alignment with, the opposite sides 16C, 16D thereof. Each first connection member 18 has a free end 18A. The second connection members 20 are laterally spaced along, and attached to and extend in second directions opposite the first directions from, the opposite end 16B of the central panel 16. The second connection members 20 are disposed substantially in parallel relationship with one another and adjacent to, and preferably in alignment with, the opposite sides 16C, 16D thereof. Each second connection member 20 has a free end 20A. The first and second pairs of connection members 18, 20 together with the central panel 16 provide the main attachment body 12 with a substantially H-shaped configuration.

The fastening means 22 permits attachment of the respective ends 18A, 20A of the first and second connection members 18, 20 to one another such that the main attachment body 12 can be wrapped around a ventilator circuit component D and held in place by the fastening means 22. Each attachment tab member 14 includes opposite first and second ends 14A, 14B and a fastening means 24. The first end 14A is mounted to the central panel 16 of the main attachment body 12 and extends along one of the pairs of connection members 18, 20. The fastening means 24 permits attachment of the second end 14B of the attachment tab member 14 to an intermediate portion of the attachment tab member 14 such that the attachment tab member 14 may be inserted through a slot E in and extended around a side of a plate F of the trach assembly B and fastened onto itself so as to hold the plate F of the trach assembly B in place in relation to the ventilator circuit component D.

Figure 3:
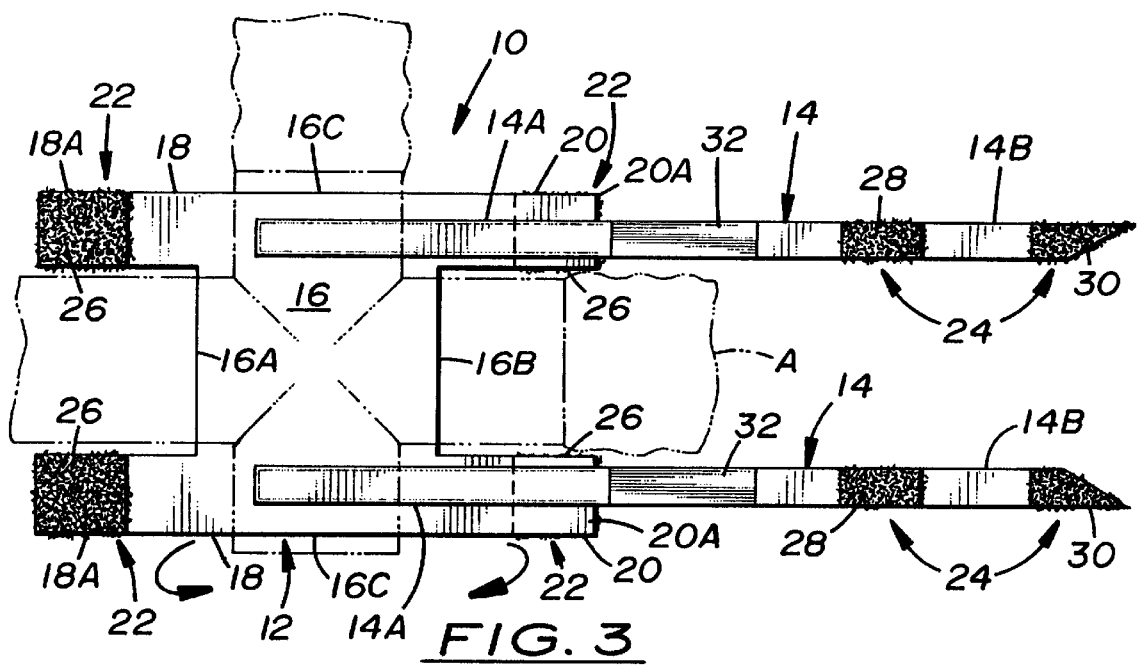
FIG. 3 is a top plan view of the holder device of FIGS. 1 and 2 with the ventilator circuit component and trach assembly plate shown in phantom line form.

More particularly, referring to FIGS. 1 to 3, the central panel 16 of the main attachment body 12 has a substantially flat and rectangular configuration, though may have any other suitable shape. The central panel 16 has a length and a width which are approximately the same. The central panel 16 also has a thickness which is substantially less than either of its length or width and is of a size such that the central panel 16 has the substantially flat configuration. The central panel 16 can be positioned against the ventilator circuit component D, such as along an underside of or at any other suitable location of the component D, as shown particularly in FIGS. 1 and 2.

Each of the first and second connection members 18, 20 of the pairs thereof of the main attachment body 12 has dimensions which are substantially the same. Also, each of the first and second connection member 18, 20 is substantially flat and has a rectangular configuration, though may have any other suitable shape. Further, each first and second connection member 18, 20 has a length which is greater than its width and a thickness which is substantially less than either of the length or width thereof and is of a size such that the first or second connection member 18, 20 has the substantially flat configuration. The thickness of the first and second connection members 18, 20 is substantially the same as the thickness of the central panel 16. The first and second connection members 18, 20 and the central panel 16 are preferably integral with one another and made from the same blank of material, though need not be so limited. Each first connection member 18 is aligned with and disposed opposite a second connection member 20 at the same side 16C or 16D of the central panel 16. Each first and second connection member 18, 20 is wrapped partially around a portion of the ventilator circuit component D. The aligned ones of the first and second connection members 18, 20 and part of the central panel 16 together wrap completely around the respective portions of the ventilator circuit component D.

The fastening means 22 of the main attachment body 12 includes a plurality of and, preferably, four patches 26 of complementary mateable hook and loop fastener material. Each patch 26 is affixed to one end 18A, 20A of one of the connection members 18, 20. The patches 26 of the first connection members 18 have the same type of fastener material, such as the hook fastener material, as shown particularly in FIG. 1, though need not be so limited. The patches 26 are also affixed to the same surface on each first connection member 18, such as that surface facing away from the one attachment tab member 14, as shown particularly in FIG. 1, though need not be so limited. The patches 26 of the second connection members 20 also have the same type of fastener material, such as the loop fastener material, as shown particularly in FIG. 1, though need not be so limited. The patches 26 are also affixed to the same surface on each second connection member 20, though need not be so limited. The surface to which the patches 26 are affixed on the first connection members 18 must be the surface opposite from the surface to which the patches 26 are affixed to the second connection members 20, as shown particularly in FIG. 1. The fastener material on the patches 26 of the second connection members 20 further are complementary to and mateable with the fastener material on the patches 26 of the first connection members 18 for attaching the first and second connection members 18, 20 to one another about the ventilator circuit component D. The dimensions of each patch 26 are substantially the same. Each patch 26 has a substantially rectangular configuration, though may have any other suitable shape. Each patch 26 also has a length and a width which are approximately the same, though need not be so limited.

Each attachment tab member 14 has dimensions which are substantially the same, though need not be so limited. Each attachment tab member 14 also is substantially flat and has a rectangular configuration, though may have any other suitable shape. Further, each attachment tab member 14 has a length which is substantially greater than its width and a thickness which is substantially less than either of the length or width thereof and is of a size such that the attachment tab member 14 has the substantially flat configuration. The thickness of the attachment tab member 14 is substantially the same as the thickness of the first and second connection members 18, 20 and the central panel 16 of the main attachment body 12. The length of each attachment tab member 14 is substantially greater than the length of each first and second connection member 18, 20 of the main attachment body 12, though need not be so limited. The width of each first and second connection member 18, 20 of the main attachment body 12 is substantially greater than the width of each attachment tab member 14, though need not be so limited.

The fastening means 24 of each attachment tab member 14 includes a pair of patches 28, 30 of complementary and mateable hook and loop fastener material. The first patch 28 is affixed at an intermediate position on the attachment tab member 14 preferably being closer to the second end 14B than to the first end 14A, though need not be so limited. The first patch 28 has one type of fastener material, such as the loop fastener material, as shown particularly in FIG. 1, though need not be so limited. The first patch 28 is affixed on one surface of the attachment tab member 14. The second patch 30 is affixed to the second end 14B of the attachment tab member 14. The second patch 30 has one type of fastener material, such as the hook fastener material, as shown particularly in FIG. 1, though need not be so limited. The second patch 30 must be affixed on the same surface as the surface upon which the first patch 28 is affixed. The second patch 30 further must have the complementary type of fastener material mateable with the fastener material on the first patch 28 for attaching portions of the attachment tab member 14 to one another once the attachment tab member 14 is inserted disposed through the slot E and around the side of the plate F of the trach assembly B. The first patch 28 has substantially the same dimensions as the second patch 30. Each of the first and second patch 28, 30 has a substantially rectangular configuration, though may have any other suitable shape. Each first and second patch 28, 30 has a length and a width which are approximately the same, though need not be so limited.

Each attachment tab member 14 also includes an elastic portion 32 at an intermediate position to permit stretching of the attachment tab member 14. The elastic portion 32 of each attachment tab member 14 is disposed centrally in the attachment tab member 14, such as between the first patch 28 and the first end 14A of the attachment tab member 14, though need not be so limited. The remainder of the attachment tab member 14 is inelastic and has an area which is greater than the area of the elastic portion 32 thereof. The elastic portion 32 permits the attachment tab member 14 to have a variety of different lengths and thereby be adaptable for different distances between the ventilator circuit component D and the trach assembly plate F.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

We claim:

1. A ventilator and tracheostomy holder device, comprising:
    (a) a main attachment body including
        (i) a central panel having opposite ends and opposite sides,
        (ii) a pair of first connection members laterally spaced apart from one another along and attached to and extending in first directions from one of said opposite ends of said central panel and disposed adjacent to said opposite sides thereof, each of said first connection members having an end,
        (iii) a pair of second connection members laterally spaced apart from one another along and attached to and extending in second directions opposite said first directions from the other of said opposite ends of said central panel and disposed adjacent to said opposite sides thereof, each of said second connection members having an end, and
        (iv) means for fastening said ends of said first and second connection members to one another such that said main attachment body will wrap around a ventilator circuit component and be held in place by said fastening means; and
    (b) at least one attachment tab member including
        (i) opposite first and second ends, said first end being mounted to said central panel of said main attachment body and extending along said connection members of one of said pairs thereof, and
        (ii) means for fastening said second end of said attachment tab member to a portion of said attachment tab member such that said attachment tab member may be inserted through a slot in and extended around a side of a plate of a tracheostomy assembly and fastened onto itself so that it may be hold the tracheostomy assembly plate in place in relation to the ventilator circuit component.

2. The holder device of claim 1 wherein each of said first connection members is disposed in alignment with one of said opposite sides of said central panel.

3. The holder device of claim 1 wherein each of said second connection members is disposed in alignment with one of said opposite sides of said central panel.

4. The holder device of claim 1 wherein said first and second of connection members and said central panel provide said main attachment body with a substantially H-shaped configuration.

5. The holder device of claim 1 wherein each of said first and second connection members of said main attachment body has substantially the same dimensions.

6. The holder device of claim 1 wherein each of said first and second connection members of said main attachment body has a length and a width and said attachment tab member has a length and a width, said length of said attachment tab member being substantially greater than said length of each of said first and second connection members of said main attachment body, said width of each of said first and second connection members of said main attachment body being substantially greater than said width of said attachment tab member.

7. The holder device of claim 1 wherein said fastening means of said main attachment body includes a plurality of patches of complementary mateable hook and loop fastener material, each of said patches being affixed to said end of one of said connection members, said patches of said first connection members having the same type of fastener material and said patches of said second connection members having the same type of fastener material complementary to and mateable with said fastener material on said patches of said first connection members.

8. The holder device of claim 1 wherein said fastening means of said attachment tab member includes a pair of patches of complementary and mateable hook and loop fastener material, a first of said patches being affixed at an intermediate position on said attachment tab member and having one type of fastener material and a second of said patches being affixed to said second end of said attachment tab member and having a complementary type of fastener material mateable with the fastener material on said first of said patches of said first connection members.

9. The holder device of claim 1 wherein said attachment tab member includes an elastic portion at an intermediate position to permit stretching of said attachment tab member.

10. The holder device of claim 9 wherein the remainder of each of said attachment tab members is inelastic and has an area greater than the area of said elastic portion of said attachment tab member.

11. The holder device of claim 1 including a pair of said attachment tab members being laterally spaced apart from one another.

12. A ventilator and tracheostomy holder device, comprising:
(a) a main attachment body including
  (i) a central panel having opposite ends and opposite sides,
  (ii) a pair of first connection members laterally spaced apart from one another along and attached to and extending in first directions from one of said opposite ends of said central panel and disposed in alignment with said opposite sides thereof, each of said first connection members having an end,
  (iii) a pair of second connection members laterally spaced apart from one another along and attached to and extending in second directions opposite said first directions from the other of said opposite ends of said central panel and disposed in alignment with said opposite sides thereof, each of said second connection members having an end, said first and second connection members together with said central panel providing said main attachment body with a substantially H-shaped configuration, and
  (iv) a plurality of patches of complementary mateable hook and loop fastener material, each of said patches being affixed to said end of one of said connection members, said patches of said first connection members having the same type of fastener material and said patches of said second connection members having the same type of fastener material complementary to and mateable with said fastener material on said patches of said first connection members such that said main attachment body may be wrapped around a ventilator circuit component and held in place by fastening said patches of complementary and mateable hook and loop fastener material on said ends of said first and second connection members to one another; and
(b) a pair of spaced apart attachment tab members, each of said attachment tab members including
  (i) opposite first and second ends, said first end being mounted to said central panel of said main attachment body and extending along one of said first and second connection members, and
  (ii) a pair of patches of complementary and mateable hook and loop fastener material, a first of said patches being affixed to an intermediate portion of said attachment tab member and having one type of fastener material and a second of said patches being affixed to said second end of said attachment tab member and having the complementary type of fastener material such that said attachment tab member may be inserted through a slot in and extended around a side of a plate of a tracheostomy assembly and fastened onto itself by fastening said patches of complementary and mateable hook and loop fastener material to one another so that it may hold the tracheostomy assembly plate in place in relation to the ventilator circuit component.

13. The holder device of claim 12 wherein each of said first and second connection members of said main attachment body has substantially the same dimensions.

14. The holder device of claim 12 wherein each of said first and second connection members of said main attachment body has a length and a width and each of said attachment tab members has a length and a width, said length of each of said attachment tab members being substantially greater than said length of each of said first and second connection members of said main attachment body, said width of each of said first and second connection members of said main attachment body being substantially greater than said width of each of said attachment tab members.

15. The holder device of claim 12 wherein each of said attachment tab members includes an elastic portion at an intermediate position to permit stretching of said attachment tab member.

16. The holder device of claim 12 wherein each of said attachment tab members has substantially the same dimensions.

17. The holder device of claim 12 wherein each of said patches of complementary mateable hook and loop fastener material of said first and second connection members of said main attachment body has substantially the same dimensions.

18. The holder device of claim 12 wherein each of said patches of complementary mateable hook and loop fastener material of said attachment tab members has substantially the same dimensions.

19. The holder device of claim 12 wherein said elastic portion of each of said attachment tab members is disposed centrally in said attachment tab member.

20. The holder device of claim 19 wherein the remainder of each of said attachment tab members is inelastic and has an area greater than the area of said elastic portion of said attachment tab member.

* * * * *